US00PP35025P3

(12) United States Plant Patent
Olesen

(10) Patent No.: US PP35,025 P3
(45) Date of Patent: Mar. 14, 2023

(54) COMPACT FLORIBUNDA ROSE PLANT NAMED 'POULPAL089'

(50) Latin Name: *Rosa hybrida*
Varietal Denomination: Poulpal089

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 17/300,610

(22) Filed: Sep. 7, 2021

(65) Prior Publication Data

US 2022/0104419 P1 Mar. 31, 2022

(30) Foreign Application Priority Data

Sep. 21, 2020 (QZ) ..... PBR 2020/2257

(51) Int. Cl.
*A01H 5/02* (2018.01)
*A01H 6/74* (2018.01)

(52) U.S. Cl.
USPC ..... Plt./141
CPC ..... *A01H 6/749* (2018.05)

(58) Field of Classification Search
USPC ..... Plt./141, 149, 150, 107, 102, 108
CPC ... A01H 5/02; A01H 5/00; A01H 6/74; A01H 6/749
See application file for complete search history.

(56) References Cited

U.S. PATENT DOCUMENTS

PP22,502 P2 * 2/2012 Olesen ..... A01H 5/02 Plt./148

OTHER PUBLICATIONS

CPVO Register version 4.1.51, retrieved on May 3, 2022 at https://online.plantvarieties.eu/publicConsultationDetails?registerId=20202257&denomination=poulpal089, 2 pp. (Year: 2022).*
Poulsen Roser A/S Xara, retrieved on May 3, 2022 at https://www.poulsenroser.dk/fr/roses/ShowProduct/60284, 3 pp. (Year: 2022).*
RHO Produktkatalog 2018, retrieved on Jul. 11, 2022 at https://www.rosenhof-odenahl.de/data/2018/01/RHO_Produktkatalog_2018.pdf, 1-2,52. (Year: 2018).*
RHO Produktkatalog Google English translation, retrieved on Jul. 11, 2022 at https://www.google.com/search?q=translation&rlz...gws-wiz, one page. (Year: 2022).*

* cited by examiner

*Primary Examiner* — June Hwu

(57) ABSTRACT

A new garden rose plant of the Compact Floribunda class which has abundant, red purple flowers and attractive foliage. This new and distinct variety has shown to be uniform and stable in the resulting generations from asexual propagation.

1 Drawing Sheet

Botanical designation: *Rosa hybrida.*
Variety denomination: 'Poulpal089'.

This application claims priority to Plant Breeder's Rights Application Number 2020/2257, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpal089', originated as a single seedling from the stated cross.

The new variety may be distinguished from its male pollen parent and female seed parent primarily by the following characteristics. The male pollen parent plant has mauve flowers while the new variety has red purple flowers. The female seed parent plant has a growth height of 40 cm, while the new variety grows to a height of 55 cm.

The objective of the hybridization of this rose variety was to create a new and distinct variety with unique qualities, such as:

1. Uniform and abundant red purple flowers;
2. Vigorous, but compact growth when propagated on its own roots;
3. Exceptional disease resistance.

This combination of qualities is not present in previously available commercial cultivars of this type, known to the inventor, and distinguish 'Poulpal089' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpal089' was selected in the spring of 2012 by the inventor as a single plant from the progeny of the aforementioned hybridization.

Asexual reproduction of 'Poulpal089' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpal089' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpal089'. Specifically illustrated in the drawing are open flowers viewed from above and the side, flower buds at various stages of development, petals detached showing reproductive flower parts and receptacle, juvenile and mature leaves and stems. Plants shown are 2 years of age.

DETAILED DESCRIPTION OF THE VARIETY

The following is a description of 'Poulpal089', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcas031', U.S. Plant Pat. No 22,502 are compared to 'Poulpal089'.

While the newly claimed plant exhibits no long prickles on the stems, 'Poulcas031' has about 7.6 mm long prickles per 10 cm of stem. Further distinguishing 'Poulpal089' from the comparison variety, the filaments for the claimed plant are Yellow-Orange Group 14A, while filaments of 'Poulcas031' are Yellow Group 12A.

Flower and Flower Bud

Blooming habit: Continuous.

Flower bud:

- *Size.*—Upon opening, 20 mm in length from base of receptacle to end of bud. Bud diameter is 15 mm.
- *Bud form.*—Urceolate.
- *Sepal inner surface.*—Color: Yellow-Green Group 146D with intonations of Greyed-Orange Group 175B. Surface: Lightly pubescent.
- *Sepal outer surface.*—Color: Yellow-Green Group 144A. Texture: Smooth.
- *Sepal shape.*—Apex: Cirrhose. Base: Flat at union with receptacle.
- *Sepal margin.*—Margins have weak foliaceous appendages on three of the five sepals.
- *Sepal size.*—7 mm long, 5 mm wide.
- *Receptacle.*—Texture: Smooth. Size: 7 mm in height, 5 mm wide. Color: Yellow-Green Group 144A. Shape: Campanulate.
- *Pedicel.*—Surface: Smooth. Length: 26 mm. Diameter: 3 mm on average. Color: Yellow-Green Group 144B and Greyed-Orange Group 175D. Strength: Strong.
- *Peduncle.*—Length: 2 to 9 cm. Diameter: About 3 mm. Color: Yellow-Green Group 144A. Texture: Smooth.

Flower bud development: Flower buds are borne in clusters of 3 to 9 flower buds per stem. Development as a panicle.

Flower bloom:

- *Fragrance.*—Moderate perfume.
- *Duration.*—The blooms have a duration on the plant of approximately 14 days. Petals fall cleanly away from plant after flowers have fully matured.
- *Size.*—Flower diameter is 75 mm when open. Flower depth is 30 mm.
- *Flower shape.*—Shallow cup.
- *Shape of flower, side view.*—The upper portion is flat convex. The lower portion is deeply concave.

Petalage: Under normal conditions, flowers have about 45 petals.

General tonality of flower: Open flowers are Red-Purple Group N66B.

Petal color:

- *Upon opening, outer petals.*—Upper surface: Red-Purple Group N66B. Lower surface: Red-Purple Group 67B.
- *Upon opening, inner petals.*—Upper surface: Red-Purple Group N66B. Lower surface: Red-Purple Group 67B.
- *Basal petal spots, upon opening.*—Upper surface: Yellow Group 4C. Lower surface: Green-Yellow Group 1C. Size: Small.
- *After opening, outer petals.*—Upper surface: Red-Purple Group N66B. Lower surface: Red-Purple Group 67B.
- *After opening, inner petals.*—Upper surface: Red-Purple Group N66B. Lower surface: Red-Purple Group 67B.
- *Basal petal spots, after opening.*—Upper surface: Green-Yellow Group 1C. Lower surface: Green-Yellow Group 1C. Size: Small.

Petals:

- *Petal reflex.*—Strong.
- *Margin.*—Entire and emarginate. No undulations.
- *Shape.*—Broad and elliptic. Apex shape: Rounded. Base shape: Acute.
- *Size.*—37 mm (l)×38 mm (w).
- *Texture.*—Smooth.
- *Thickness.*—Average.

Reproductive flower parts:

- *Pollen.*—None observed.
- *Anthers.*—Size: 2 mm in length. Color: Yellow Group 4B. Quantity: 35 to 40 average.
- *Filaments.*—Color: Yellow-Orange Group 14A. Length: 3 mm.
- *Pistils.*—Length: 6 mm. Quantity: 30 on average.
- *Stigmas.*—Color: Greyed-Yellow Group 160D.
- *Styles.*—Color: White Group 155A with intonations of Red-Purple Group N57C.
- *Location of stigmas.*—Inferior in location relative to the length of the filaments and the height of the anthers.
- *Hips.*—None Observed.

Plant

Plant growth: Upright, very compact, and well branched. Plants are 55 cm in height, and 40 cm wide.

Stems:

- *Color of juvenile growth.*—Yellow-Green Group 146C with intonations of Greyed-Orange Group 176B.
- *Color of mature growth.*—Yellow-Green Group 146D.
- *Length.*—Canes are about 18 cm from the base of the plant to the flowering portion.
- *Diameter.*—About 6 mm.

*Internodes.*—On mature canes about 25 mm between nodes.

*Surface Texture.*—Young wood: Smooth. Older wood: Smooth.

Long prickles: None observed.

Plant foliage:

*Compound leaf.*—105 mm (l)×80 (w).

*Quantity.*—3 to 4 leaves per 10 cm of stem on average.

*Leaf bearing angle to the stem.*—45 degrees.

*Color of juvenile foliage.*—Upper and lower side: Yellow-Green Group N144A with intonations of Greyed-Orange Group 175B.

*Color of mature foliage.*—Upper side: Yellow-Green Group 146A. Lower side: Yellow-Green Group 147C.

Plant leaves and leaflets:

*Stipules.*—Size: 20 mm long, mm wide. Quantity: 2 per compound leaf. Shape: Linear, slightly broad based with outward extending apices. Margins: Finely serrated. Color: Yellow-Green Group 144A.

*Petiole.*—Length: 25 mm. Diameter: 2 mm. Upper surface color: Yellow-Green Group 144A. Lower surface color: Yellow-Green Group 144A.

*Rachis.*—Length: 41 mm. Upper surface color: Yellow-Green Group 144A. Lower surface color: Yellow-Green Group 144A.

*Leaflet.*—Quantity: 5 to 7 leaflets. Margins: Serrated. Undulations absent. Size: Terminal leaflets are about 50 mm long, 41 mm wide. Shape: Generally elliptical. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulpal089', substantially as illustrated and described herein, due to its abundant red purple flowers, disease resistance, and extended period of bloom.

* * * * *

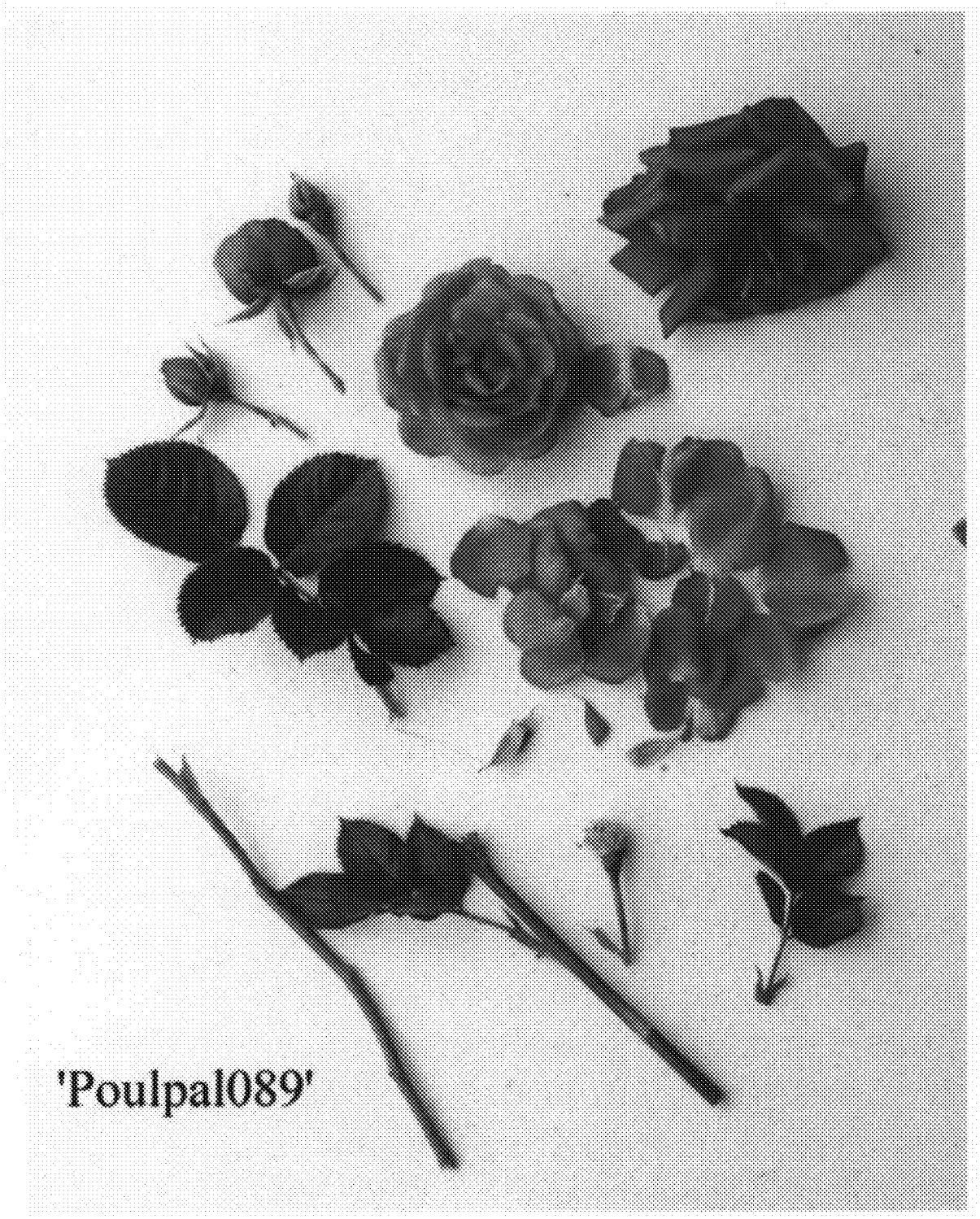
'Poulpal089'